United States Patent [19]

Imbert et al.

[11] Patent Number: 4,986,818

[45] Date of Patent: Jan. 22, 1991

[54] SYRINGE ASSEMBLY

[75] Inventors: Claude Imbert, La Tronche; Jean M. Jouet, Meylan; Patrick Carre, Voiron, all of France

[73] Assignee: Becton, Dickinson and Company, Franklin Lakes, N.J.

[21] Appl. No.: 502,607

[22] Filed: Mar. 30, 1990

[51] Int. Cl.$^5$ .............................................. A61M 5/32
[52] U.S. Cl. ...................................... 604/192; 604/263
[58] Field of Search ............... 604/192, 263, 187, 198, 604/110, 111, 197, 199

[56] References Cited

U.S. PATENT DOCUMENTS

| | | | |
|---|---|---|---|
| 3,865,236 | 2/1975 | Rycroft | 206/364 |
| 4,317,446 | 3/1982 | Ambrosio et al. | |
| 4,430,082 | 2/1984 | Schwabacher | 604/263 |
| 4,636,201 | 1/1987 | Ambrose et al. | 604/192 |
| 4,816,024 | 3/1989 | Sitar et al. | 604/192 |
| 4,872,552 | 10/1989 | Unger | 604/263 X |
| 4,911,693 | 3/1990 | Paris | 604/192 |

Primary Examiner—John D. Yasko
Attorney, Agent, or Firm—John L. Voellmicke

[57] ABSTRACT

A syringe assembly includes a barrel having an open proximal end, a chamber for retaining fluid and a tip portion extending from a distal end of the barrel having a passageway therethrough communicating with the chamber. A needle cannula having a distal end extends outwardly from the tip portion and includes a lumen in fluid communication with the passageway. A needle shield assembly includes a resilient needle sheath having an open proximal end, a closed distal end, a sidewall defining a receptacle therein and an annular flange extending radially outwardly from the proximal end of the needle sheath. The needle sheath is positioned within an elongate rigid shield having an open proximal end, a distal end and a sidewall therebetween. Structure for holding the sheath within the shield includes a flange-receiving aperture in the needle shield sidewall adjacent to the open proximal end. The aperture includes a ledge on its proximal side for engaging the proximal side of the flange for holding the sheath in the shield. Structure is also provided for deflecting the annular flange causing more of the annular flange to project into the flange-receiving aperture than if the structure were not included. The needle shield assembly is positioned with the distal end of the cannula engaging the cannula sealing distal end of the sheath and the proximal end of the sheath removably engages the tip portion of the barrel to hold the shield assembly on the barrel while simutaneously sealing the lumen of the cannula.

21 Claims, 4 Drawing Sheets

SYRINGE ASSEMBLY

BACKGROUND OF THE INVENTION

1. Field of the Invention.

The present invention relates to a hypodermic syringe assembly, and more particularly concerns a hypodermic syringe suitable for prefilling including a needle shield assembly having cannula sealing features and features to help prevent accidental needle sticks.

2. Description of the Prior Art.

Many injectable medications are packaged and distributed in the hypodermic syringe that will eventually be used to administer the medication to the patient. Prefilled syringes are available from pharmaceutical manufacturers, and syringes are frequently prefilled in hospital pharmacies. In both instances, the prefilled syringe is subject to a variety of environmental challenges during storage, shipping and/or handling before the medication is administered to the patient. Accordingly, the contents of the syringe must be sealed to preserve their sterility.

Articles such as hypodermic syringe tip caps are sometimes used to seal the distal tip of a prefilled hypodermic syringe. Syringes having a permanently attached needle cannula can be sealed with a resilient needle shield as taught in U.S. Pat. No. 3,865,236 to Rycroft. Rycroft teaches a needle shield of resilient rubber closed at one end and adapted to be positioned in surrounding relationship with respect to the needle so as to normally maintain the needle in a sealed atmosphere. The needle shield of Rycroft seals the cannula so that the prefilled medication is not in fluid communication with the environment.

Resilient rubber needle shields such as those taught by Rycroft are widely used and accepted. However, in recent years there has developed an increased concern regarding the transfer of disease and/or infection to syringe users and healthcare professionals who accidentally stick themselves with hypodermic needles while preparing, using or disposing of a hypodermic syringe products. Placing an excessive force on the tip of a syringe and needle assembly having a resilient rubber needle shield may cause the needle to penetrate the needle shield to expose the sharp injection point. Although reshielding is neither preferred nor recommended by many people, circumstances arise where it is necessary or convenient for the user to reshield the needle after injection. A resilient needle shield can present a potential problem if it is reshielded improperly so that the needle pierces the sidewall of the needle shield or the distal end of the needle shield and sticks the user. Syringe assemblies having rigid plastic needle shields avoid some of these problems but are generally not suitable for prefilled glass syringes because they do not have the ability to seal the needle cannula and because o their hardness and relative inelasticity may not effectively attach to the tip of a glass syringe barrel which in some manufacturing processes has a much broader range of tolerances than the tip of a plastic syringe.

One way to retain the positive and desirable features of the resilient needle shield and to reduce the potential for accidental needle sticks is to provide a hard plastic protector or cover which can be installed over the needle assembly having a barrel with fixed needle cannula and a resilient needle shield in place such as an already prefilled hypodermic syringe assembly. U.S. Pat. No. 4,430,082 to Schwabacher teaches an inflexible hollow cylindrical sleeve which fits over an elastomeric protective needle cover. The cylindrical sleeve is provided with flexible gripping means which when depressed exerts pressure on the inner elastomeric protective cover thereby allowing the cover to be removed along with the protective cylindrical sleeve. Although the teachings of Schwabacher provide an improvement the device still has shortcomings with respect to prevention of accidental needle sticks. After the rigid cover is applied to the syringe assembly it can be removed leaving the needle covered only by the elastomeric protecting cover, effectively returning the device to its original state, before the rigid sleeve was installed, having all the shortcomings recited for syringe assemblies without rigid needle sleeves.

A similar device is taught by Ambrosio et al. in U.S. Pat. No. 4,317,446. Ambrosio et al. teach a plunger rod/protector which fits over a elastomeric needle sheath on a prefilled syringe having a fixed needle cannula. The plunger rod/protector of Ambrosio et al. does not engage the sheath and maintains its position on the syringe assembly by engaging the outer surface of the syringe barrel so that the plunger rod protector can be installed and removed from the distal end of the syringe without removing the elastomeric needle sheath. Ambrosio et al. has the disadvantages of Schwabacher in that the plunger rod protector may be removed leaving the sharp needle covered only by the elastomeric needle sheath.

A further improvement is taught by Ambrose et al. in U.S. Pat. No. 4,636,201. Ambrose et al. teach a rigid sheath cover adapted to be placed over a rubber needle cover on a hypodermic syringe. The rigid sheath cover has a plurality of spaced cantilever like teeth projecting outwardly from the tubular body of the cover to form the open end. At least two of the teeth include a lip projecting inwardly toward the center of the opening formed by the teeth for gripping the needle cover after installation. The apparent advantage of Ambrose et al. over the devices of Ambrosio et al. and Schwabacher is that after installation it appears that the rubber needle cover will remain within the rigid sheath. However, the spaced teeth of the Ambrose et al. sheath cover must be flexible enough to deform while passing over a soft rubber needle cover to the final assembled position. If the teeth are very rigid they may not flex enough to pass over the rubber needle cover or tear the cover in the process of assembly. Accordingly, the Ambrose et al. device must perform a balancing act between having cantilever teeth which are flexible enough for proper installation yet strong enough to retain the rubber needle cover after assembly. Also, if the teeth are too weak they may break away from the needle shield during assembly or use.

Shields for sealing the contents of a prefilled hypodermic syringe and protecting the needle from the environment have been addressed by the prior art. Improvements involving rigid covers and protectors which can be installed on a prefilled syringe having a resilient needle sheath have also been addressed by the prior art. However, there is still a need for a simple, straight forward, reliable, easily fabricated hypodermic syringe assembly having a needle shield assembly which retains the cannula sealing and cleanliness protecting features of the resilient needle sheath and incorporates a rigid shield to help prevent accidental needle sticks during the assembly and operation and disposal of the syringe.

There is also a need for a simple, one piece rigid needle shield which retains the resilient needle sheath without the use of cantilever elements or other spring like members wherein said needle shield is structured to help prevent the disassembly of the needle shield and the resilient needle sheath.

SUMMARY OF THE INVENTION

The hypodermic syringe of the present invention comprises an elongate barrel having an open proximal end, a chamber for retaining fluid and a tip portion extending from a distal end of the barrel having a passageway therethrough communicating with the chamber. A needle cannula having a distal end extending outwardly from the tip portion includes a lumen therethrough in fluid communication with the passageway. A needle shield assembly includes a resilient needle sheath having an open proximal end, a closed distal end, a sidewall defining a receptacle therein and an annular flange extending radially outwardly from the proximal end of the needle sheath. The resilient needle sheath is positioned within an elongate rigid needle shield having a continuous open proximal end, a distal end and a sidewall therebetween defining a needle shield longitudinal axis. Means for holding the sheath within the shield is provided so that the sheath cannot be removed from the shield during normal use of the syringe assembly. The holding means includes a flange receiving aperture in the needle shield sidewall adjacent to the open proximal end. The aperture has a ledge on its proximal side for engaging the proximal side of the needle sheath flange for holding the sheath in the shield. The holding means also includes means for contacting and deflecting the annular flange causing more of the annular flange to project into the flange receiving aperture than if the deflecting means were not included. The sheath includes cannula sealing means at the distal end of the receptacle for providing a fluid tight seal between the lumen and the environment of the syringe assembly. The needle shield assembly is positioned with the distal end of the cannula engaging the cannula sealing means and the proximal end of the sheath removably engaging the tip portion of the barrel to hold the needle shield assembly on the barrel while simultaneously sealing the lumen of the cannula so that the sheath surrounds the entire portion of the cannula which extends outwardly from the tip portion. The needle shield assembly is easily engageable and removable from the barrel and the cannula using manual force applied to the shield.

In accordance with another embodiment of the present invention, a hypodermic syringe assembly comprises an elongate barrel having an open proximal end, a chamber for retaining fluid and a tip portion extending from a distal end of the barrel having a passageway therethrough communicating with the chamber. A needle cannula having a distal end extending outwardly from the tip portion includes a lumen therethrough in fluid communication with the passageway. A needle shield assembly includes a resilient needle sheath having an open proximal end, a closed distal end, a sidewall defining a receptacle therein, and an annular flange extending radially outwardly from the proximal end of the needle sheath. The needle sheath is positioned within an elongate rigid needle shield having a continuous open proximal end, a distal end and a sidewall therebetween defining a needle shield longitudinal axis. Means for holding the sheath within the shield is provided so that the sheath cannot be removed from the shield during normal use of the syringe assembly. The holding means includes a plurality of flange-receiving apertures in the needle shield sidewall adjacent to the open proximal end of the needle shield. Each of the apertures includes a ledge on the proximal side of the aperture for engaging the proximal side of the flange for holding the needle sheath in the shield. The holding means also includes means for contacting and deflecting the annular flange causing more of the annular flange to project into the flange-receiving apertures than if the deflecting means were not included. The means for contacting and deflecting the flange include a plurality of inwardly projecting protuberances on the sidewall positioned adjacent to the proximal end of the needle shield and between the apertures. The resilient sheath includes cannula sealing means at the distal end of the receptacle for providing a fluid tight seal between the lumen and the environment of the syringe assembly. The needle shield assembly is positioned with the distal end of the cannula engaging the cannula sealing means and the proximal end of the sheath removably engaging the tip portion to hold the shield assembly on the barrel while simultaneously sealing the lumen of the cannula so that the sheath surrounds the entire portion of the cannula which extends outwardly from the tip portion. The shield and the sheath are structured so that the shield can be manually assembled to the sheath while the sheath is properly positioned sealing the cannula and engaging the tip portion of the barrel. The needle shield assembly is easily engageable and removable from the barrel and the cannula using manual force applied to the needle shield.

DETAILED DESCRIPTION

While this invention is satisfied by embodiments in many different forms, there is shown in the drawings and will herein be described in detail a preferred embodiment of the invention with the understanding that the present disclosure is to be considered exemplary of the principles of the invention and is not intended to limit the scope of the invention to the embodiment illustrated. The scope of the invention will be measured by the appended claims and their equivalents.

Adverting to FIGS. 1-12, a preferred hypodermic syringe assembly 20 includes an elongate substantially cylindrical syringe barrel 21 having an open proximal end 22, a chamber 23 for retaining fluid and a tip portion 25 extending from a distal end 27 of the barrel having a passageway 28 therethrough communicating with the chamber.

For the purposes of the description of the present invention, the term "distal end" is meant to refer to the end furthest from the person holding the syringe, whereas the term "proximal end" is meant to refer to the end closest to the holder of the syringe.

A needle cannula 29 having a distal end 31 including a sharpened point 32 extends outwardly from tip portion 25. Needle cannula 29 includes a lumen 33 therethrough in fluid communication with passageway 28.

A stopper 34 is slidably positioned in fluid tight engagement inside the barrel and is adapted to engage a plunger rod 35 to facilitate its operation. In this embodiment, the stopper contains an internal thread (not shown) which engages an external thread (not shown) on the plunger rod. The plunger rod is accessible outside of the proximal end of the barrel and is provided to move the stopper along the barrel to force fluid into and out of the chamber through the passageway. Specifically, the stopper is capable of moving fluid from chamber 23 through the passageway upon its movement toward distal end 27 of the barrel. The stopper is capable of facilitating the drawing of fluid into the chamber through the passageway upon its movement away from the distal end. Disc shaped plunger rod flange 37 is provided as a convenient structure for applying forces to move the plunger rod with respect to the barrel. A stopper flange 38 on the plunger rod is provided to supply a large surface area to transmit force from the plunger rod to the stopper in a direction toward the stopper, without damaging the stopper. The plunger rod may be installed when the syringe is assembled, or may be provided as a separate component which is engaged to the stopper at the time of use. It will be apparent to one skilled in the art that numerous constructions can be used to join a stopper and a plunger rod and that the arrangement described above is exemplary of these many possibilities. Also, it is within the purview of this invention to include a one-piece plunger rod-stopper assembly.

A medicament such as liquid medication 39 is contained within the chamber between the stopper and the distal end of the barrel. Medicaments such as solid or powder medication may be contained in the chamber. When solid or powdered medications are used, a diluent must be drawn into the chamber to mix with the medication before injection.

An important feature of the instant invention, representing a substantial improvement over the prior art, is needle shield assembly 40 which includes a resilient needle sheath 41 having an open proximal end 43, a closed distal end 44, a sidewall 45 defining a receptacle 46 therein. The needle sheath also includes a projection extending outwardly from proximal end 43. In this preferred embodiment the projection is an annular flange 47 positioned at the proximal end of the sheath. The resilient needle sheath is positioned within an elongate rigid shield 51 having a continuous open proximal end 52, a distal end 53 and a sidewall 55 therebetween defining a needle shield longitudinal axis 57.

A shortcoming of some prior art devices is that the rigid cover may be removed from the resilient needle cover after assembly. When a needle and barrel assembly having a resilient cover installed, with the rigid cover removed, is being handled or used there exists the potential danger of accidental needle sticks. The presence of a rigid cover at this time would reduce the potential danger. Without the rigid cover pressure on the resilient cover can cause the needle to protrude through the resilient cover. It should also be noted that without a rigid cover the needle with flexible cover can be bent or damaged by external forces applied to the flexible cover. A bent needle is believed to be a potential danger because the sharp needle point is not directed along the axis of the barrel as the user assumes it is.

It is an object of this invention to provide a rigid needle shield that may be assembled with a resilient needle sheath either separately or after the sheath is installed on a needle and barrel assembly. This dual ability will allow the use of the rigid needle shield of the instant invention to be used in existing manufacturing processes. The rigid needle shield may be installed in a step which is in addition to and after the installation of the resilient needle sheath.

It is also an objective of this invention to provide a needle shield assembly having a resilient sheath and a rigid shield structured wherein the sheath cannot be removed from the shield during normal use of the product and preferably the sheath should not be capable of removal without the use of tools and with the specific intent to dismantle and possibly destroy the needle shield assembly. To this end, means for holding the sheath within the shield are provided so that the sheath cannot be removed from the shield during normal use of the syringe assembly. The holding means includes at least one flange receiving aperture in the needle shield. In this preferred embodiment the holding means includes two flange receiving apertures 58 in needle shield sidewall 55 adjacent to continuous open end 52. Each aperture is rectangularly shaped and includes a ledge 59 on the proximal side of the aperture for engaging proximal side 49 of the flange for holding resilient needle sheath 41 in rigid needle shield 51.

Figure 1:
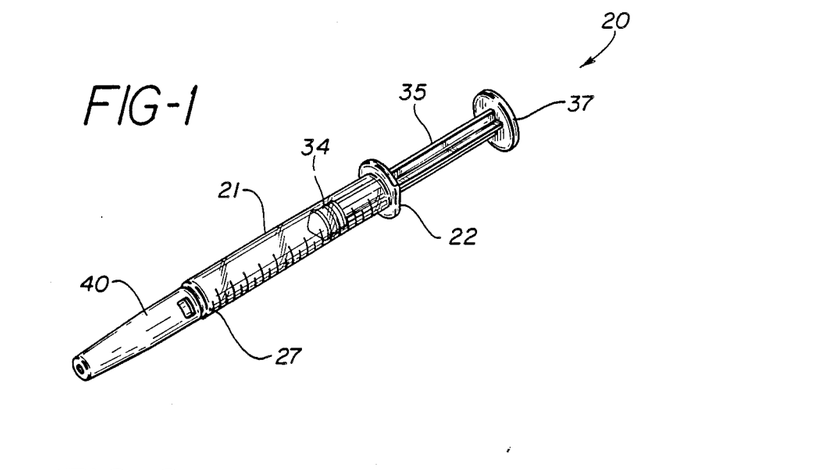
FIG. 1 is a perspective view of the preferred embodiment of the hypodermic syringe assembly of the present invention.
Figure 2:
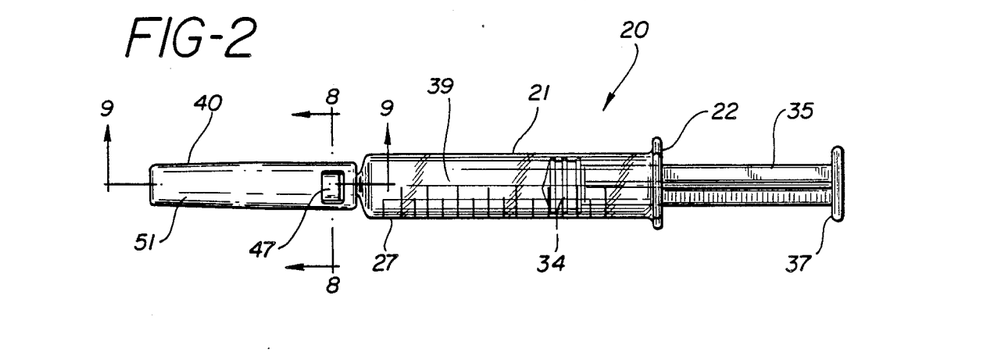
FIG. 2 is a side elevation view of the syringe assembly of FIG. 1.
Figure 3:
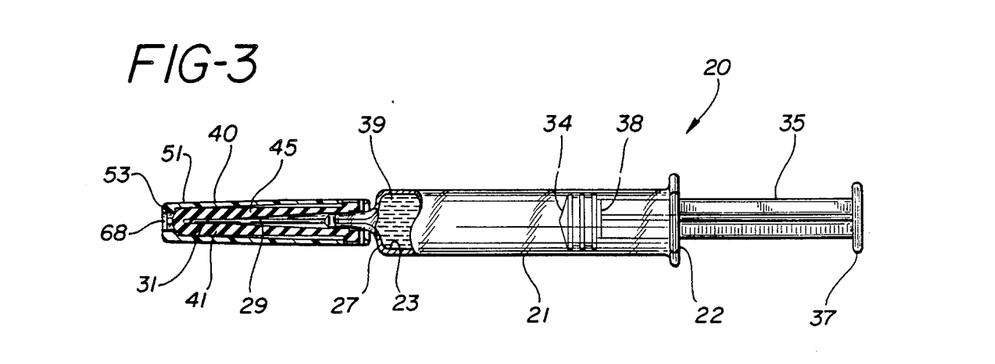
FIG. 3 is a partial cross-sectional view of the syringe assembly of FIG. 1.
Figure 4:
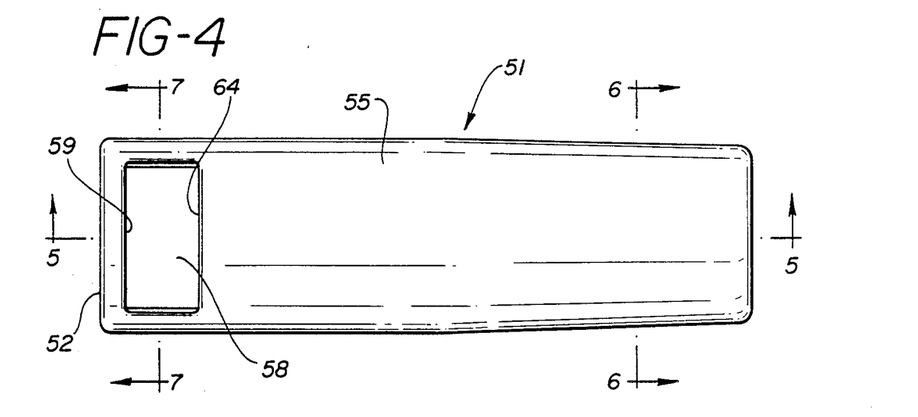
FIG. 4 is an enlarged side elevation view of the rigid needle shield of the syringe of FIG. 1.
Figure 5:
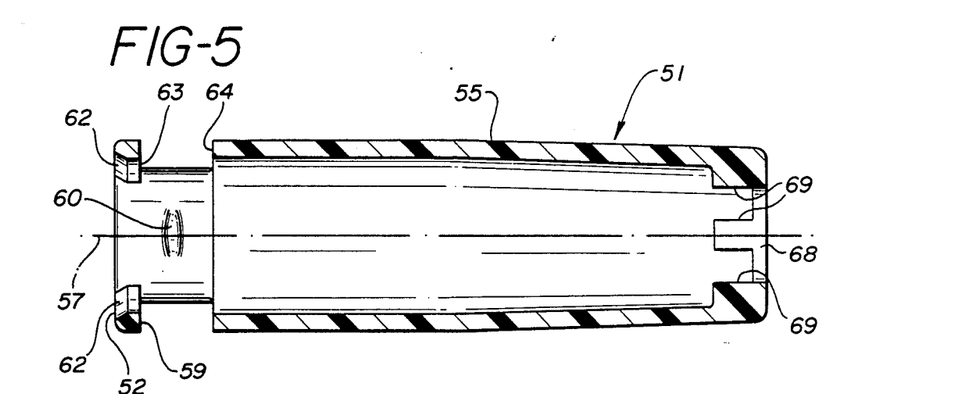
FIG. 5 is a cross-sectional view of the needle shield of FIG. 4 taken along line 5—5.
Figures 6, 7:
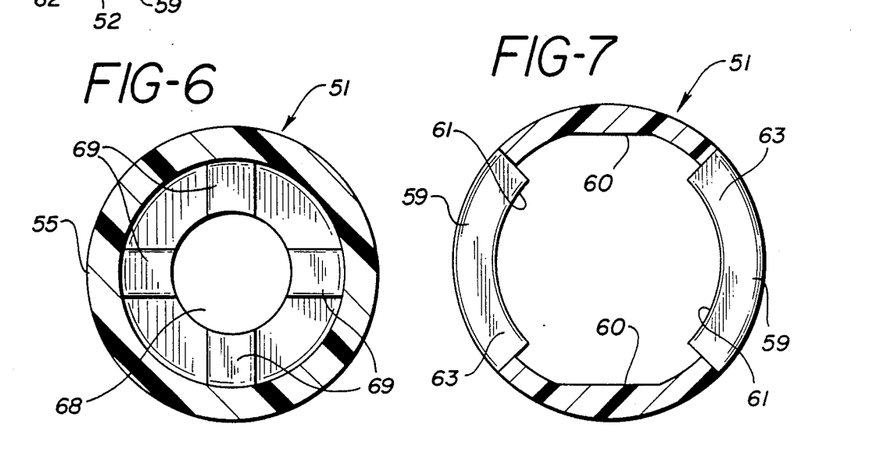
FIG. 6 is a cross-sectional view of the needle shield of FIG. 4 taken along line 6—6.
FIG. 7 is a cross-sectional view of the needle shield of FIG. 4 taken along line 7—7.
Figure 8:
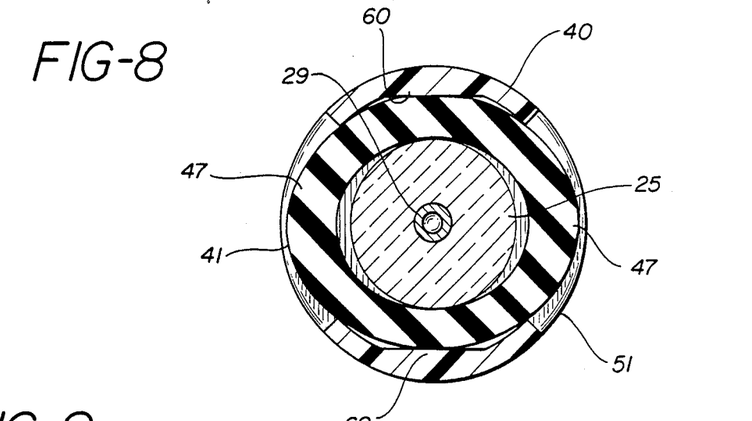
FIG. 8 is an enlarged cross-sectional view of the syringe assembly of FIG. 2 taken along line 8—8.

The holding means also includes deflecting means for contacting the annular flange causing more of the annular flange to project into flange-receiving apertures 58 than if the deflecting means were not provided. In this preferred embodiment the holding means includes deflecting means for contacting and deflecting annular flange 47 causing more of the annular flange to project into flange-receiving apertures 58 than if the deflection means were not provided. In this preferred embodiment a deflecting means for contacting and deflecting the flange includes two inwardly projecting protuberances 60 on sidewall 55 positioned adjacent to proximal end 52 of the needle shield and between apertures 58. Protuberances 60 are opposed from each other as best illustrated in FIG. 7 so that the protuberances deflect flange 47, as best illustrated in FIG. 8, forcing the flange into a non circular shape such as the slightly oval or elliptical shape produced by the protuberances in this preferred embodiment. The pressure applied by the protuberances which are spaced apart a distance less than the diameter of the flange cause portions of the flange which are perpendicular to the line of action of the protuberances to bulge and extend more fully and completely into the apertures. The action of the protuberances and the apertures to retain the resilient sheath flange is an important feature of the present invention. This structure provides for easy assembly of the resilient sheath and rigid shield while also providing for the aggressive retention of the sheath in the shield by changing the effective diameter of the flange during the assembly process.

Prior art needle shields attempt to provide for easy assembly of the sheath in the shield along with adequate retention forces to keep the assembly together by designing a rigid sheath to be flexible, such as taught by Ambrose et al. in U.S. Pat. No. 4,636,201. The result is a more complicated intricate needle shield with spring like cantilevers projecting from its proximal end. The device of Ambrose et al. deals with the compromise between insertion forces and retention forces by adjusting the flexibility of the most rigid member of the combination of the needle shield and sheath. Because the needle shield is substantially more rigid it is believed to be more sensitive to variations in tolerances in the manufacturing process and, accordingly, the more difficult component to control. The needle shield assembly of the instant invention does not attempt to adjust the resiliency of the rigid shield but relies on the inherent resiliency of the needle sheath while taking advantage of the rigidity of the needle shield rather than attempting to compromise its rigidity.

The syringe assembly of this preferred embodiment also includes two wedge-shape projections 61 projecting inwardly from the proximal end of the needle shield sidewall between the proximal end of the shield and apertures 58. Each of the projections includes a cam surface 62 extending distally and inwardly and terminating at a top surface 63 oriented transversely to longitudinal axis 57 of the needle shield and extending into aperture ledges 59. Projections 61 are shaped so that upon assembly needle sheath flange 47 is compressed as it passes along cam surfaces 63 and snaps into apertures 58 when the flange passes top surfaces 63.

It should be noted that the instant invention does not require special and different techniques with respect to the removal or replacement of the needle shield assembly because the sheath and the shield once assembled are assembled together at all times during operation and disposal of the syringe.

The interaction of the distal side 50 of flange 47 and the distal edge 64 of apertures 58 performs another important function in that it maintains the relative position of the sheath with respect to the shield during installation of the needle shield assembly onto the barrel and needle assembly. The interaction between distal side 50 of the flanges and distal edges 64 of the apertures helps to force the sheath over the tip portion of the barrel to form a preferably air-tight interference fit between the resilient sheath and the rigid tip portion of the barrel.

It is also preferred that the structure of the needle sheath and needle shield be such that manual disassembly of these components, after assembly, is extremely difficult without the use of tools.

Figure 9:
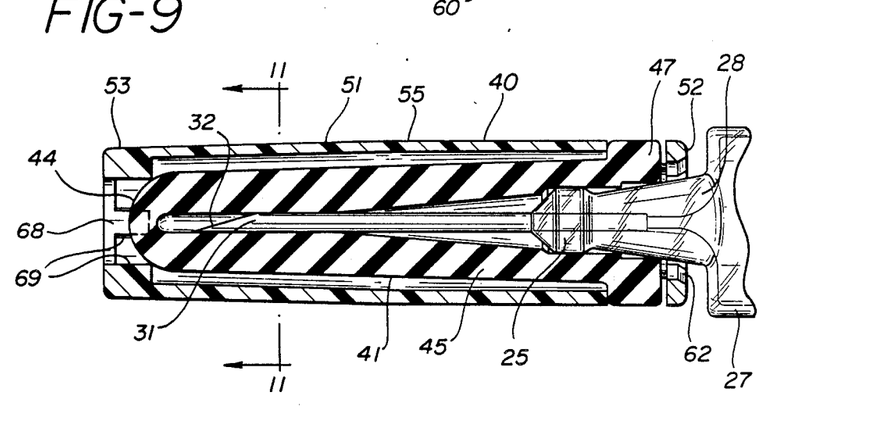
FIG. 9 is an enlarged partial cross sectional view of the syringe assembly of FIG. 2 taken along line 9—9.
Figure 10:
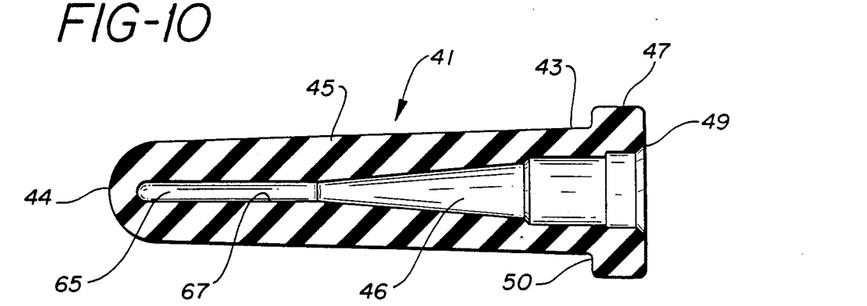
FIG. 10 is an enlarged cross sectional view of the resilient needle sheath of the needle shield assembly of the syringe of FIG. 1.
Figure 11:
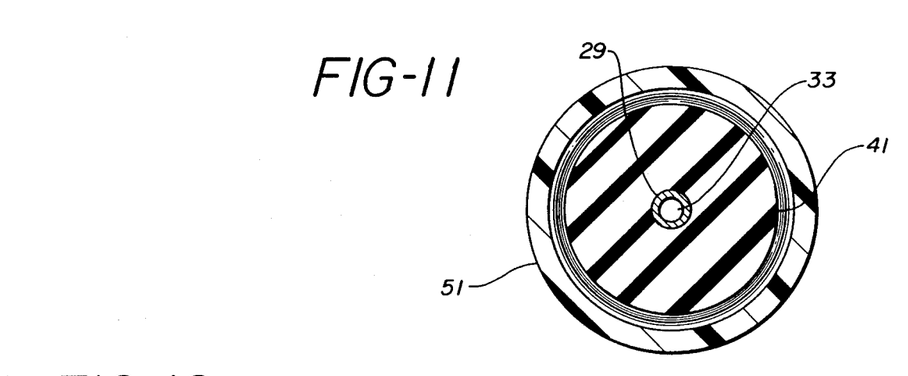
FIG. 11 is a cross-sectional view of the syringe assembly of FIG. 9 taken along line 11—11.
Figure 12:
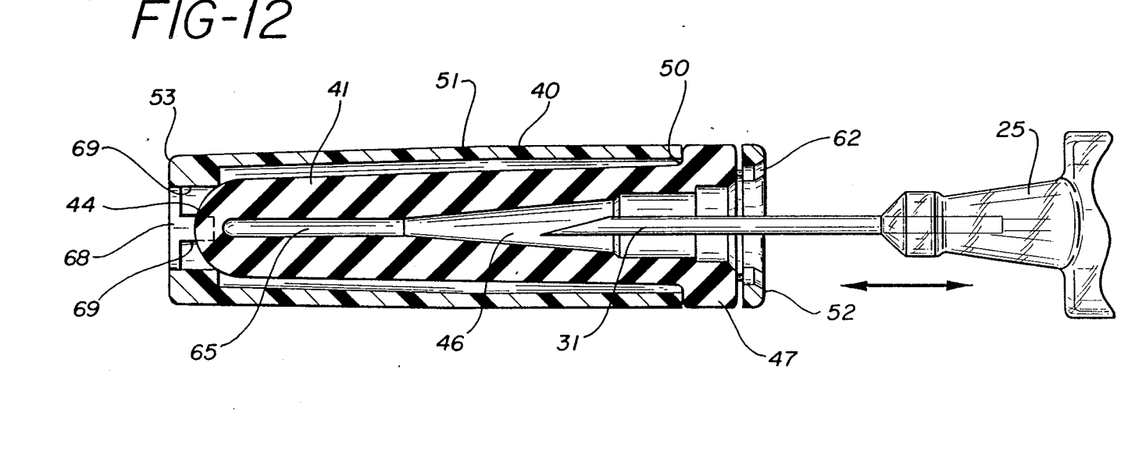
FIG. 12 is the syringe assembly of FIG. 9 illustrating the needle shield assembly being partially removed from the syringe barrel and needle assembly.

The resilient sheath of the present invention also includes cannula sealing means at the distal end of receptacle 46 for providing a fluid tight seal between lumen 33 and the environment of the syringe assembly. In this preferred embodiment the cannula sealing means includes an elongate retention conduit 65 having a sidewall 67 adapted to accept distal end 31 of the cannula in a fluid-tight engagement between the outside of the cannula and the conduit sidewall as best illustrated in FIGS. 9 and 11. In this preferred embodiment the elongate retention conduit includes a circularly shaped cross section portion having a diameter less than the outside diameter of the cannula.

In this preferred embodiment a lubricant is provided on the cannula to reduce the forces required for the cannula to penetrate an injection vial or a patient's flesh. This lubricant may also enhance the assembly of the needle shield assembly to the syringe barrel and needle assembly by facilitating the engagement of the cannula 29 into elongate retention conduit 65.

Needle shield assembly 40 is positioned with distal end 31 of cannula 29 engaging cannula elongate retention conduit to seal the cannula lumen and proximal end 43 of the sheath removably engaging and sealing the interface between the sheath and the tip portion of the barrel so that the resilient sheath surrounds the entire portion of the cannula which extends outwardly from the tip portion. The sealing of the cannula contains the medicament within the syringe barrel and protects it from the environment, and the sealing of the area around the tip portion covers and protects the cleanliness of the exterior portions of the cannula and in the preferred embodiment is intended to protect the sterility of the cannula. It is an important feature of the instant invention that one continuous element, the resilient sheath, seals the cannula and the exterior of the tip portion to protect the cleanliness and sterility of the cannula. Multiple components to perform these functions may present problems with respect to leaking or providing an ineffective seal which may not protect cleanliness and/or sterility of the cannula. It is also within the purview of the instant invention to include cannula sealing means wherein the length of the receptacle within the needle sheath and the cannula are chosen so that when the needle shield assembly is properly positioned on the tip portion of the barrel, the sharp point of the distal end of the cannula is embedded in the distal end of the sheath with portions of the sheath occluding the lumen of the cannula. This structure does not require a cannula retention conduit since the sealing of the cannula is accomplished by embedding the tip of the cannula into the resilient distal end of the needle sheath.

The needle shield assembly is easily removed from the barrel and cannula using manual force applied to the shield. Using care it may be reassembled in the same fashion to protect persons coming in contact with the syringe assembly from accidental needle sticks.

In this embodiment rigid shield 51 includes aperture 68 at its distal end. The aperture is provided to facilitate sterilization by allowing sterilizing gases or steam to access the interior of the needle shield assembly. An aperture may also provide to aid in the assembly of the needle sheath and distal portion of the shield. If the outside diameter of the sheath approaches the inside diameter or shape of the rigid shield assembly of the parts may tend to trap air which can escape through aperture 68. It is within the purview of the instant invention to provide multiple apertures at the distal end or in other portions of the rigid shield. It is also within the purview of the instant invention to provide a rigid shield having an aperture at the distal end which is substantially coincident with the inside diameter of the shield at the distal end so that the distal end is open.

Rigid needle shield 51 of this preferred embodiment also includes inwardly facing ribs 69 in the distal end of the needle shield to help prevent the needle sheath from occluding vent aperture 68.

After the needle shield assembly is removed, the remaining portion of the hypodermic syringe assembly may be used to inject medication into a patient using known safe techniques. If the needle shield assembly is installed onto the barrel and needle assembly after injection, the rigid shield of the preferred embodiment helps prevent accidental needle sticks by providing a rigid shield structure.

The syringe barrel may be constructed of a wide variety of materials such as metals, plastics and ceramics. Glass is preferred due to its transparency, low moisture vapor transmission rate and compatibility with many medication formulations. The needle shield of the instant invention is especially desirable for glass syringes because the resilient needle sheath is more capable of engaging a glass syringe barrel tip which in some manufacturing processes is subject to broader dimensional tolerances than metal or injection molded plastic barrel tip portions.

A wide variety of materials such as natural rubber, synthetic rubber, thermoplastic elastomers and thermoplastics are suitable for the shield with natural rubber being preferred. More rigid materials, such as thermoplastics, are more suitable for embodiments where a cannula tip is not embedded in the distal end of the needle shield because of the potential for the more rigid material to damage the sharp cannula point. A wide variety of materials, such as natural rubber, synthetic rubber and thermoplastic elastomers are suitable for the stopper with natural rubber and butyl rubber being preferred. A wide variety of medical grade lubricants are suitable for use in lubricating the needle cannula with medical grade silicone lubricants such as Dow Corning CD360, a dimethyl polysiloxane silicone lubricant. A wide variety of materials such as thermoplastics, thermosetting plastics and metals or combinations thereof are suitable for the shield. Injection moldable thermoplastics are preferred. It is preferred that the needle cannula be sterile at the time of use. Accordingly, materials should be chosen for compatibility with the sterilization process being used.

Thus, the present invention provides a straight forward, reliable, easily fabricated syringe having a needle shield assembly which retains the cannula sealing and cleanliness protecting features of the resilient needle sheath, and incorporates a rigid shield to help prevent accidental needle sticks during assembly and operation and disposal of the syringe. The present invention also provides a simple one-piece rigid needle shield which retains the resilient needle sheath without the use of cantilever elements or other spring-like members wherein the needle shield is structured to help prevent the disassembly of the needle shield and the resilient sheath.

What is claimed is:

1. A hypodermic syringe assembly comprising:
   an elongate barrel having an open proximal end, a chamber for retaining fluid and a tip portion extending from a distal end of said barrel having a passageway therethrough communicating with said chamber;
   a needle cannula having a distal end extending outwardly from said tip portion including a lumen therethrough in fluid communication with said passageway;
   a needle shield assembly including a resilient needle sheath having an open proximal end, a closed distal end, a sidewall defining a receptacle therein and an annular flange extending radially outwardly from said proximal end, said resilient needle sheath being positioned within an elongate rigid needle shield having a continuous open proximal end, a distal end and a sidewall therebetween defining a needle shield longitudinal axis;
   means for holding said sheath within said shield so that said sheath cannot be removed from said shield during normal use of said syringe assembly, said holding means including a flange receiving aperture in said needle shield sidewall adjacent to said open proximal end, said aperture having a ledge on the proximal side of said aperture for engaging the proximal side of said flange for holding said sheath in said shield, said holding means also including deflecting means for contacting and deflecting said annular flange causing more of said annular flange to project into said flange receiving aperture than if said deflecting means were not included;
   said sheath including cannula sealing means at said distal end of said receptacle for providing a fluid-tight seal between said lumen and the environment of said syringe assembly;
   said needle shield assembly being positioned with said distal end of said cannula engaging said cannula sealing means and said proximal end of said sheath removably engaging said tip portion to hold said shield assembly on said barrel while simultaneously sealing said lumen of said cannula so that said sheath surrounds the entire portion of said cannula which extends outwardly from said tip portion; and
   said needle shield assembly being easily engageable to and removable from said barrel and said cannula using manual force applied to said shield.

2. The hypodermic syringe assembly of claim 1 wherein said shield and said sheath are structured so that said shield can be manually assembled to said sheath while said sheath is properly positioned sealing said cannula and engaging said tip portion of said barrel.

3. The hypodermic syringe assembly of claim 1 wherein said cannula sealing means includes an elongate retention conduit having a sidewall adapted to accept said distal end of said cannula in fluid tight engagement between the outside of said cannula and said conduit sidewall.

4. The hypodermic syringe assembly of claim 3 wherein said retention conduit includes a circularly shaped cross section portion having a diameter which is less than the outside diameter of said cannula.

5. The hypodermic syringe assembly of claim 1, wherein said sealing means includes said cannula being long enough so that when said needle shield assembly is positioned on said tip portion said distal end of said cannula is embedded in said closed distal end of said sheath with portions of said sheath occluding said lumen.

6. The hypodermic syringe assembly of claim 1 wherein said deflecting means for contacting and deflecting said flange includes an inwardly projecting protuberance on said sidewall adjacent to said proximal end of needle shield.

7. The hypodermic syringe assembly of claim 1 further including a wedge-shaped projection projecting inwardly from the proximal end of said needle shield sidewall between said open proximal end and said aperture, said projection having a cam surface extending distally and inwardly and terminating adjacent to a top surface oriented transversely to the longitudinal axis of said needle shield and extending into said aperture ledge so that upon assembly said needle sheath flange is compressed as it passes along said cam surface and snaps into said aperture when said flange passes said top surface.

8. The hypodermic syringe assembly of claim 1 having two flange receiving apertures in opposed relationship on said needle shield sidewall.

9. The hypodermic syringe assembly of claim 8 wherein said deflecting means for contacting and deflecting said flange includes two inwardly projecting protuberances on said sidewall positioned adjacent to said proximal end of said needle shield and between said apertures.

10. The hypodermic syringe assembly of claim 1 further including two wedge shaped projections projecting inwardly from the proximal end of said needle shield sidewall between said open proximal end and said aperture, said projections having a cam surface extending distally and inwardly and terminating adjacent to a top surface oriented transversely to said longitudinal axis of said needle shield and extending into said aperture ledges so that upon assembly said needle sheath flange is compressed as it passes along said cam surfaces and snaps into said apertures when said flange passes said top surfaces.

11. The hypodermic syringe assembly of claim 1 further including a vent aperture in said distal end of said needle shield.

12. The hypodermic syringe assembly of claim 11 further including an inwardly facing rib in said distal end of said needle shield to help prevent said sheath from occluding said vent aperture.

13. The hypodermic syringe assembly of claim 1 wherein said needle shield is made of integral one piece construction.

14. The hypodermic syringe assembly of claim 1 further including a stopper slidably positioned in fluid tight engagement inside said barrel adapted to engage a plunger rod to facilitate its operation, said stopper capable of moving fluid from said chamber through said passageway upon its movement toward said distal end, said stopper capable of facilitating the drawing of fluid into said chamber through said passageway upon its movement away from said distal end.

15. The hypodermic syringe assembly of claim 14 further including medicament within said chamber between said stopper and said distal end of said barrel.

16. The hypodermic syringe assembly of claim 14 further including a plunger rod engaged to said stopper and extending outwardly from said proximal end of said barrel.

17. The hypodermic syringe assembly of claim 1 wherein said sheath is made from material selected from the group consisting of natural rubber, synthetic rubber and thermoplastic elastomers.

18. The hypodermic syringe assembly of claim 1 wherein said shield is made of rigid material selected from the group consisting of thermoplastic, thermosetting plastic, metals and combinations thereof.

19. The hypodermic syringe assembly of claim 1 wherein said barrel is made of glass.

20. A hypodermic syringe assembly comprising:

an elongate barrel having an open proximal end, a chamber for retaining fluid and a tip portion extending from a distal end of said barrel having a passageway therethrough communicating with said chamber;

a needle cannula having a distal end extending outwardly from said tip portion including a lumen therethrough in fluid communication with said passageway;

a needle shield assembly including a resilient needle sheath having an open proximal end, a closed distal end, a sidewall defining a receptacle therein, and an annular flange extending radially outwardly from said proximal end, said resilient needle sheath being positioned within an elongate rigid needle shield having a continuous open proximal end, a distal end and a sidewall therebetween defining a needle shield longitudinal axis;

means for holding said sheath within said shield so that said sheath cannot be removed from said shield during normal use of said syringe assembly, said holding means including a plurality of flange receiving apertures in said needle shield sidewall adjacent to said open proximal end, each of said apertures having a ledge on the proximal side of said aperture for engaging the proximal side of said flange for holding said sheath in said shield, said holding means also including deflecting means for contacting and deflecting said annular flange causing more of said annular flange to project into said flange receiving apertures than if said deflecting means were not included, said means for contacting and deflecting said flange including a plurality of inwardly projecting protuberances on said sidewall positioned adjacent to said proximal end of said needle shield and between said apertures, said sheath including cannula sealing means at said distal end of said receptacle for providing a fluid-tight seal between said lumen and the environment of said syringe assembly;

said needle shield assembly being positioned with said distal end of said cannula engaging said cannula sealing means and said proximal end of said sheath removably engaging said tip portion to hold said shield assembly on said barrel while simultaneously sealing said lumen of said cannula so that said sheath surrounds the entire portion of said cannula which extends outwardly from said tip portion;

said shield and said sheath being structured so that said shield can be manually assembled to said sheath while said sheath is properly positioned sealing said cannula and engaging said tip portion of said barrel; and said needle shield assembly being easily engageable to and removable from said barrel and said cannula using manual force applied to said shield.

21. The hypodermic syringe assembly of claim 20 further including a plurality of wedge shaped projections projecting inwardly from the proximal end of said needle shield sidewall between said open proximal end and said aperture, each of said projections having a cam surface extending distally and inwardly and terminating adjacent to a top surface oriented transversely to said longitudinal axis of said needle shield and extending into said aperture ledges so that upon assembly said needle sheath flange is compressed as it passes along said cam surfaces and snaps into said apertures when said flange passes said top surfaces.

* * * * *